United States Patent [19]

Garlick, Jr. et al.

[11] Patent Number: 5,192,529

[45] Date of Patent: Mar. 9, 1993

[54] LOW STRINGING TOOTHPASTE

[75] Inventors: Theodore H. Garlick, Jr., Litchfield; Philip E. Miner, Newtown, both of Conn.

[73] Assignee: Chesebrough-Pond's USA Co., Division of Conopco, Inc., Greenwich, Conn.

[21] Appl. No.: 892,294

[22] Filed: Jun. 2, 1992

[51] Int. Cl.⁵ .................... A61K 7/16; A61K 7/18
[52] U.S. Cl. ........................... 424/49; 424/52; 424/57
[58] Field of Search ...................... 424/49-58

[56] References Cited

U.S. PATENT DOCUMENTS

| | | | |
|---|---|---|---|
| 3,689,637 | 9/1972 | Pader | 424/52 |
| 4,022,881 | 5/1977 | Hawking | 424/52 |
| 4,435,380 | 3/1984 | Pader | 424/49 |
| 4,485,089 | 11/1984 | Leipold | 424/49 |
| 4,565,692 | 1/1986 | Mulvey et al. | 424/52 |
| 4,584,189 | 4/1986 | Leipold | 424/54 |

FOREIGN PATENT DOCUMENTS 56-147709 11/1981 Japan.
61-218513 9/1986 Japan.
87-015523 4/1987 Japan.

Primary Examiner—Shep K. Rose
Attorney, Agent, or Firm—Milton L. Honig

[57] ABSTRACT

A dentifrice composition is provided that includes a polyol present as a humectant, an abrasive to clean teeth and a thickener system consisting of a low viscosity sodium carboxymethyl cellulose and a low viscosity hydroxyethyl cellulose. Preferably the dentifrice is in gel form and has the advantage of low stringiness and good phase stability.

10 Claims, No Drawings

LOW STRINGING TOOTHPASTE

BACKGROUND OF THE INVENTION

1. Field of the Invention

The invention relates to a dentifrice composition for cleaning teeth.

2. The Related Art

Dentifrice compositions for promoting the health and appearance of the mouth, and especially of the teeth and gums, are well-known. Such compositions generally contain polishing agents, humectants and thickeners.

A problem in formulating the typical components of dentifrices is that of providing proper texture. Special problems arise when the polishing agent is based upon a silica abrasive. Upon extrusion from the tube, a dentifrice must retain body. Too frequently, however, the extruded segment slumps. There is poor cohesion. From its perch atop the brush, the dentifrice rapidly spreads forth drooping down into the bristles. A related problem is that elegant toothpastes are expected to break sharply upon extrusion from the tube. The ribbon should not string out; it should have shortness of texture.

A still further problem of dentifrices, especially of those of the clear gel variety, is that of separation and shrinking of solids from the paste matrix. Fluids as a result exude from the matrix eventually leading to collapse and a brick-like solid results. The phenomenum is known as weeping.

In U.S. Pat. No. 3,689,637, a method is described whereby improved shortness of texture is obtained by incorporating polyethylene glycol of appropriate molecular weight into the dentifrice. Although ameliorative of the problem, polyethylene glycol does not achieve sufficient shortness of texture necessary in such dentifrice formulations as silica-based gels. Moreover, the solution is costly.

Accordingly, it is an object of the present invention to provide a dentifrice that exhibits relatively low stringiness, good cohesion and minimizes the problem of weeping.

Another object of the present invention is to provide a dentifrice that is in the form of a silica-based gel having good clarity but low stringiness and being free of weeping.

These and other objects of the present invention will become more apparent by consideration of the following summary, detailed description and examples.

SUMMARY OF THE INVENTION

A dentifrice composition is provided comprising:
(i) a polyol present in an effective amount to function as a humectant;
(ii) an abrasive present in an effective amount to polish teeth; and
(iii) a thickener system comprising:
   (a) a low viscosity carboxymethyl cellulose gum; and
   (b) a low viscosity hydroxyethyl cellulose gum, the amount of the carboxymethyl cellulose and hydroxyethyl cellulose being present in a weight ratio of about 5:1 to about 1:5.

DETAILED DESCRIPTION

It has been discovered that a low stringing and relatively nonweeping dentifrice can be achieved with a thickener system combination of low viscosity carboxymethyl cellulose gum and low viscosity hydroxyethyl cellulose gum. Product stringiness using this combination was found to be unexpectedly less than for identical formulations using a medium-high viscosity carboxymethyl cellulose gum alone.

According to the invention, the first critical component of the thickener system is a carboxymethyl cellulose (hereinafter CMC) of low viscosity having at 4% concentration in water at 25° C. a viscosity that ranges from about 50 to about 500 cps, preferably from about 80 to about 300 cps, as measured on a Brookfield Viscometer utilizing Spindle No. 2, Spindle Speed 60 rpm at factor 5. Advantageously, the CMC will have a degree of substitution ranging from about 0.65 to about 0.95. The most preferred CMC is one designated 7L2P available from the Aqualon Company. Molecular weight (intrinsic viscosity determination) will range from about 50,000 to about 200,000, optimally about 90,000.

The second critical component of the thickener system is that of a low viscosity hydroxyethyl cellulose (hereinafter HEC). This gum will exhibit a viscosity ranging from about 75 to about 200 cps preferably between 100 and 150 cps, at 25° C. when dissolved at 5% in water and measured with a Brookfield Viscometer utilizing Spindle No. I, Spindle Speed 30 rpm at factor 2. Molecular weight (as determined by intrinsic viscosity) will range from about 20,000 to about 200,000, optimally around 90,000. Advantageously, the degree of substitution may range from about 0.5 to about 3.0, but optimally is about 2.5. The most suitable commercially available gum is Natrosol 250L available from the Aqualon Company.

Amounts of each of the gums may range anywhere from about 0.01 to about 1.5%, preferably from about 0.1 to about 1%, optimally between about 0.15 and 0.75% by weight. Relative weight ratios of the CMC to HEC may range from about 5:1 to about 1:5, preferably between about 3:1 and about 1:3.

A humectant and water system will normally be included in dentifrices of the present composition. Humectants are polyols which may include glycerol, sorbitol, propylene glycol, lactitol, xylitol, polyethylene glycol, hydrogenated corn syrup and mixtures thereof. Most advantageously, systems of this invention will exclude polyethylene glycol and substitute therefore glycerol, sorbitol and/or a small amount of hydrogenated corn syrup. Generally the amount of humectant will range from about 25 to about 90%, preferably from about 40 to 70% by weight.

The most important nonhumectant component in toothpastes are abrasives. The abrasives useful in the dentifrice compositions presently disclosed must have certain properties. These must include high cleaning and polishing activity, ability to form a clear gel, and safety for use in the mouth. Any abrasive possessing these three properties may be combined with the humectant in the present invention.

Abrasives which are especially useful in clear dentifrices are the silica xerogels described in Pader et al, U.S. Pat. No. 3,538,230. In fact, silica xerogels are the abrasives of choice for use in clear dentifrices and are the preferred abrasives in the present invention. Silica xerogels yield dentifrice compositions which result in surprisingly good cleaning and polishing characteristics when applied topically to the teeth. In addition, silica xerogels produce a high luster without excessive enamel or dentin abrasion. These silicas are also highly compatible with most common dentifrice ingredients, including oral health agents, and may be formulated to produce transparent or translucent pastes.

More specifically, the silica xerogels useful in the present dentifrice compositions are synthetic, amorphous, porous silica xerogels having an average particle diameter in the range from about 2 to about 30 microns, preferably in the range from about 3 to about 15 microns.

Silica xerogels suitable for use in clear dentifrice compositions are commercially available. One suitable xerogel is marketed under the trade name Syloid 63X. This material has an average particle diameter of about 8 to 10 microns.

Other suitable silicas include Syloid 63, which has an average particle diameter of about 5 microns, Syloid 73, which has an average particle diameter of about 5 microns, Syloid 63XX, which has an average particle size of about 10 microns, and Syloid 404, which has an average particle diameter of about 6 microns. All of the above silica xerogels in the Syloid series are available from W. R. Grace, Davison Chemical Division.

Another class of abrasive materials suitable for use in the present dentifrice compositions is the class of silicas known as precipitated silicas. Those precipitated silicas that are applicable are, in the broadest terms, prepared by the admixture of a mineral acid and sodium silicate solution to form a precipitate followed by washing, drying and milling of the precipitate. The products are amorphous, hard particles which can be made with differing degrees of abrasivity. One such precipitated silica is disclosed by Wason, U.S. Pat. No. 4,272,509. Another type of precipitated silica which can be used, but which has only limited abrasive properties, is disclosed by Watson, U.S. Pat. No. 3,864,470. The description of precipitated silicas and the methods of their preparation are disclosed in U.S. Pat. Nos. 4,272,509 and 3,684,470. A most preferred commercially available precipitated silica is Zeo 49 available from the J. M. Huber Corporation, Chemicals Division.

The amount of abrasive is limited to those amounts which safely provide good polishing and cleaning and which, when combined with common toothpaste ingredients of a nonabrasive nature, will give a smooth, flowable, not excessively gritty, acceptable tasting toothpaste. This amount generally lies in the range of about 5% to about 50% by weight of the total dentifrice. The preferred range is from about 6 to about 35% and the most preferred range is about 7 to about 25% by weight of the dentifrice.

The amount of water present in compositions of the invention may be at any level that leads to transparent or translucent compositions. Generally, the amount of water will range from about 5% to about 60%, preferably between about 10 and 35%, optimally between about 15 and 30% by weight.

Surfactants are normally also included in compositions according to the present invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

Tartar control agents may be incorporated into compositions of this invention, especially effective will be agents containing phosphorous. Inorganic phosphorous tartar control agents may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tartar control agents include zinc citrate and polyphosphonates such as disodium ethane-1-hydroxy-1,1-diphosphonate (EHDP), methanediphosphonic acid, and 2-phosphonobutane-1,2,4-tricarboxylic acid.

For anticaries protection, a source of fluoride ion will normally be present in the second component of the dentifrice composition. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anticaries agent will be present in an amount from about 0.05 to about 3% by weight, preferably 0.2 to 1% by weight of the second component.

Sweetening agents such as sodium saccharin, sodium cyclamate, Acesulfam K, aspartame, sucrose and the like may be included at levels from about 0.1 to 5% by weight.

Other additives may also be incorporated including preservatives, silicones, other synthetic or natural polymers such as Gantrez S-97, and antigingivitis actives such as trichlosan.

Furthermore, where it is desired to have an opaque toothpaste, titanium dioxide or some opacifier agent may be incorporated into the otherwise transparent or translucent gel.

The following examples will more fully illustrate the embodiments of this invention. All parts, percentages and proportions referred to herein and in the appended claims are by weight unless otherwise indicated.

EXAMPLE 1

Typical of the present invention is a clear gel toothpaste having the formulation outlined in Table I.

TABLE I

| Ingredient | Wt. % |
|---|---|
| Polyol II | 65.7 |
| Syloid 63X | 10.0 |
| Syloid 244 | 9.5 |
| Glycerol | 5.0 |
| Sodium Lauryl Sulfate | 1.5 |
| SD Alcohol 38B | 1.3 |
| Sodium Monofluorophosphate | 0.8 |
| Flavor | 0.7 |
| Sodium CMC 7L2P | 0.6 |
| Sodium Saccharin | 0.3 |
| Natrosol 250L | 0.2 |
| Sodium Benzoate | 0.08 |
| Colorant | 0.007 |
| Water | qs |

Preparation of the above formula is done in the standard manner such as described in U.S. Pat. No. 4,453,979 (DeMasi et al).

EXAMPLE 2

The following Examples detail experiments investigating the effect of various types and grades of co-thickeners (binders) used in conjunction with 0.6% sodium CMC 7L2P. Except for the gum system, the formulation as listed under Table I was the basic toothpaste tested in combination with various thickeners. Table II details viscosity and molecular weights for these thickeners. Tables III and IV list the effect of these thickeners on cohesiveness and stringiness, respectively.

Evaluations utilized an Instron Tensile Tester wherein the sampled toothpaste was placed between two 1-inch round plates having a 4.0 mm gap. As the two plates separate, the toothpaste resists deformation. The force in grams required to pull the plates apart is noted as the measure of cohesion. The length in millimeters traveled by the Instron crosshead necessary for breakage of the toothpaste strand is noted as the measure of stringiness. For instance, a nonstringy sample would have a low travel value. Beyond the first separation or pull, three additional pulls were performed on each sample to see how the material reacted to additional shear. All measurements were computer controlled. A sample size of 6 for each formula was utilized.

250L, 250M, 250HH), only the one of low viscosity did not get substantially stringier with increasing shear. Consequently, the gum of choice was Natrosol 250L exhibiting a stable/nonseparating paste while having low stringiness that did not become significantly stringier upon additional shear.

EXAMPLE 3

This Example illustrates the effect that various CMC gums have upon stringiness and cohesion properties. Natrosol 250L was maintained at a constant level of 0.2% in combination with various types of CMC gums according to the base formula of Example 1. Table V details viscosity ranges for the CMC gums evaluated. Results of the Instron Tensile Tester are reported under

TABLE II

Identity and Physical Properties of the Gums

| Gum | Cellulose Derivative Type | Brookfield Viscosity (cps at 25° C.*) | | Molecular Weight |
|---|---|---|---|---|
| Natrosol 250M | Hydroxyethyl | 4,000–6,500 | (2%) | 850,000 |
| Natrosol 250L | Hydroxyethyl | 75–150 | (5%) | 95,000 |
| Natrosol 250H | Hydroxyethyl | 1,500–3,000 | (1%) | 1,150,000 |
| Natrosol 250HH | Hydroxyethyl | 3,400–5,000 | (1%) | 1,300,000 |
| Natrosol Plus 330 CS | Hydroxyethyl (modified)** | 150–500 | (1%) | 300,000 |
| Klucel EF | Hydroxypropyl | 200–600 | (10%) | 80,000 |
| Methocel E4M | Hydroxypropyl methyl | 4,000 | (2%) | 86,000 |
| Benecel MO42 | Hydroxyethyl methyl | 20,000 | (2%) | 800,000 |
| CMC 9M31XF | Carboxymethyl | 1,500–3,100 | (2%) | 250,000 |

*Numbers in ( ) are gum weight concentration in water
**Low molecular weight polymer modified with a long chain hydrophobic alkyl group

TABLE III

Effect of Gum System Components on Cohesive Force

| Formula | Gum A* | Gum B** | Cohesive Force, grams |
|---|---|---|---|
| A | Natrosol 250 M | CMC7L2P | 30.7 ± 1.7 |
| B | Natrosol 250L | CMC7L2P | 33.3 ± 0.8 |
| C | Natrosol 250H | CMC7L2P | 31.2 ± 1.1 |
| D | Natrosol 250HH | CMC7L2P | 31.6 ± 1.0 |
| E | Natrosol Plus 330 CS | CMC7L2P | 30.5 ± 0.6 |
| F | Klucel EF | CMC7L2P | 28.3 ± 1.2 |
| G | Methocel E4M | CMC7L2P | 28.2 ± 1.1 |
| H | Benecel MO42 | CMC7L2P | 26.1 ± 0.7 |
| I | — | CMC 9M31XF | 44.1 ± 2.1 |

*Gum A was employed at 0.2%
**Gum B was employed at 0.6%, except for last entry which was at 0.4%.

The results listed under Table III indicated that Formula B had (except for control Formula I) the best cohesive value. Formula B utilized a combination of low viscosity HEC and CMC gums.

TABLE IV

Effect of Gum System Components on Stringiness

| | Stringiness (mm) as Function of Number of Pulls | | | |
|---|---|---|---|---|
| Formula | 1 | 2 | 3 | 4 |
| A | 35.2 ± 1.2 | 39.3 ± 1.3 | 36.3 ± 1.7 | 38.7 ± 2.7 |
| B | 38.2 ± 0.9 | 36.9 ± 1.5 | 46.1 ± 3.0 | 50.1 ± 3.6 |
| C | 41.5 ± 2.1 | 40.3 ± 1.6 | 44.7 ± 2.1 | 47.5 ± 4.3 |
| D | 36.1 ± 1.7 | 36.9 ± 2.3 | 48.0 ± 3.2 | 52.6 ± 3.1 |
| E | 48.8 ± 2.6 | 45.2 ± 2.1 | 51.0 ± 4.6 | 51.7 ± 1.3 |
| F | 42.8 ± 1.9 | 38.8 ± 1.7 | 41.1 ± 3.1 | 45.1 ± 2.7 |
| G | 41.3 ± 1.7 | 43.5 ± 0.7 | 40.4 ± 2.5 | 38.7 ± 3.8 |
| H | 47.9 ± 2.8 | 47.7 ± 1.6 | 56.1 ± 4.3 | 56.6 ± 2.3 |
| I | 53.0 ± 4.7 | 53.3 ± 2.3 | 53.3 ± 2.8 | 54.4 ± 1.7 |

Toothpaste incorporating Methocel E4M, Klucel EF and Benecel MO42 were all unstable. Liquid separated from these toothpastes within three months of storage. From Table IV it is seen that by itself CMC 9M31XF, i.e. medium viscosity grade, had the highest stringiness value. Of the three least stringy samples (Natrosol Table VI.

TABLE V

Viscosity of Various CMC Gums

| Type | Brookfield Viscosity (cps at 25° C.*) | |
|---|---|---|
| 7LF | 25–50 | (2%) |
| WALOCEL CRT 30 PA | 20–40 | (2%) |
| 7MF | 400–800 | (2%) |
| 7L2P | 50–200 | (4%) |
| 7M8SF | 200–800 | (2%) |
| 9M8F | 400–800 | (2%) |
| 12M8P | 400–800 | (2%) |
| 7H3SF | 1,000–2,800 | (1%) |
| 12M31P | 800–3,100 | (2%) |
| 9M31XF | 1,500–3,100 | (2%) |
| 7H4F "Non-deaerated" | 2,500–6,000 | (1%) |
| 9H4F "Non-deaerated" | 2,500–6,000 | (1%) |
| 7HF | 1,500–3,000 | (1%) |

*Numbers in ( ) are gum weight concentration in water.

TABLE VI

Effect of Various CMC Gums on Stringiness

| | Stringiness (mm) as Function of Number of Pulls | | | |
|---|---|---|---|---|
| Formula | 1 | 2 | 3 | 4 |
| 7LF | 40.6 ± 3.6 | 40.2 ± 1.5 | 43.3 ± 1.2 | 43.4 ± 1.8 |
| WALOCEL CRT30PA | 35.2 ± 1.1 | 43.3 ± 1.0 | 43.1 ± 1.3 | 44.6 ± 0.7 |
| 7MF | 35.6 ± 1.8 | 39.6 ± 2.1 | 41.1 ± 1.8 | 46.4 ± 1.6 |
| 7L2P | 32.7 ± 0.3 | 38.9 ± 0.6 | 36.2 ± 0.5 | 37.9 ± 1.2 |
| 7M8SF | 37.9 ± 1.5 | 38.3 ± 2.5 | 46.1 ± 3.1 | 46.1 ± 2.1 |
| 9M8F | 33.2 ± 0.6 | 36.7 ± 0.9 | 40.7 ± 0.3 | 42.3 ± 0.9 |
| 12M8P | 35.3 ± 0.8 | 40.8 ± 1.3 | 43.9 ± 1.0 | 45.6 ± 1.5 |
| 7H3SF | 47.5 ± 0.9 | 43.8 ± 2.6 | 56.7 ± 1.7 | 61.3 ± 3.0 |
| 12M31P | 41.2 ± 0.2 | 44.1 ± 1.1 | 45.6 ± 1.8 | 46.6 ± 0.9 |
| 9M31XF | 43.9 ± 1.8 | 47.7 ± 2.1 | 50.0 ± 0.9 | 57.3 ± 2.6 |
| 7H4F "Non-deaerated" | 43.1 ± 1.3 | 43.4 ± 1.9 | 43.7 ± 1.1 | 44.3 ± 1.7 |
| 9H4F "Non-deaerated" | 37.4 ± 2.0 | 40.9 ± 0.8 | 41.0 ± 1.1 | 43.2 ± 1.7 |
| 7HF | 41.1 ± 1.8 | 43.4 ± 2.0 | 45.1 ± 1.1 | 45.6 ± 1.6 |

Based on results of Table VI, it is evident that CMC 7L2P and 9M8F have the lowest stringiness both after 1 and 4 pulls. The toothpaste with CMC 7H3SF was the stringiest, over 45% stringier after the first pull and over 60% stringier than the 7L2P paste after the fourth pull.

Table VII sets forth the cohesive force values as measured on the Instron Tensile Tester. The best value was obtained for CMC 7LF, the low viscosity grade gum.

TABLE VII

| CMC | Cohesive Force, Grams |
| --- | --- |
| 7LF | 52.2 ± 2.7 |
| WALOCEL CRT 30 PA | 56.3 ± 3.6 |
| 7MF | 68.1 ± 1.7 |
| 7L2P | 69.1 ± 1.1 |
| 7M8SF | 73.8 ± 0.9 |
| 9M8F | 76.4 ± 2.6 |
| 12M8P | 79.0 ± 3.1 |
| 7H3SF | 86.2 ± 2.7 |
| 12M31P | 90.8 ± 4.5 |
| 9M31XF | 94.8 ± 1.2 |
| 7H4F "Non-deaerated" | 96.6 ± 0.8 |
| 9H4F "Non-deaerated" | 96.9 ± 2.7 |
| 7HF | 101.4 ± 1.1 |

The foregoing description and Examples illustrate selected embodiments of the present invention. In light thereof, various modifications will be suggested to one skilled in the art, all of which are within the spirit and purview of this invention.

What is claimed is:

1. A low-stringiness and relatively nonweeping toothpaste compositions comprising:
   (i) a polyol present in an effective amount to function as a humectant;
   (ii) an abrasive present in an effective amount to polish teeth; and
   (iii) a thickener system comprising:
      (a) a low viscosity carboxymethyl cellulose gum having a viscosity ranging from about 50 to about 500 cps when 4% is placed in water at 25° C.; and
      (b) a low viscosity hydroxyethyl cellulose gum having a viscosity ranging from about 75 to about 200 cps when 5% is placed in water at 25° C., the amount of the carboxymethyl cellulose and hydroxyethyl cellulose being present in a weight ratio of about 5:1 to about 1:5, said toothpaste having good cohesion and sufficient shortness of texture so as not to become significantly stringier upon additional shear, and upon extrusion retains body without stringiness, slump, separation, shrinking, collapse or weeping.

2. The composition according to claim 1 wherein the ratio of carboxymethyl cellulose to hydroxyethyl cellulose ranges from about 3:1 to about 1:3.

3. The composition according to claim 1 wherein the polyol is exclusively selected from the group consisting of glycerol, hydrolyzed polysaccharide, sorbitol, and combinations thereof with water.

4. The composition according to claim 1 wherein the abrasive is a silica.

5. The composition according to claim 1 which is in a clear gel form.

6. The composition according to claim 1 wherein the carboxymethyl cellulose gum has a viscosity ranging from about 80 to about 300 cps when 4% is placed in water at 25° C.

7. The composition according to claim 1 wherein the hydroxyethyl cellulose gum has a viscosity ranging from about 100 to about 150 cps when 5% is placed in water at 25° C.

8. The composition according to claim 1 wherein the humectant is present in an amount from 25 to about 90% by weight.

9. The composition according to claim 1 wherein the abrasive is present in an amount from about 5 to about 50% by weight.

10. The composition according to claim 5 wherein is present an effective amount of an opacifier to render the otherwise clear gel opaque.

* * * * *